United States Patent [19]

Bujanowski et al.

[11] Patent Number: 5,403,580
[45] Date of Patent: Apr. 4, 1995

[54] ORGANOSILICON GELS AND METHOD OF MAKING

[75] Inventors: Valerie J. Bujanowski; Dimitris E. Katsoulis; Maris J. Ziemelis, all of Midland, Mich.

[73] Assignee: Dow Corning Corporation, Midland, Mich.

[21] Appl. No.: 643,638

[22] Filed: Jan. 22, 1991

[51] Int. Cl.$^6$ ............................ A61K 7/32; A61K 9/10
[52] U.S. Cl. .................................. 424/65; 424/484; 424/486; 514/944; 252/315.4
[58] Field of Search ................. 424/65, 66, 67, 68; 514/944; 552/266, 544, 542; 252/315.4

[56] References Cited

U.S. PATENT DOCUMENTS

| | | | |
|---|---|---|---|
| 4,781,917 | 11/1988 | Luebbe et al. | 424/67 |
| 4,790,961 | 12/1988 | Weiss | 260/376 |
| 4,954,333 | 9/1990 | Ward | 424/66 |

Primary Examiner—Thurman K. Page
Attorney, Agent, or Firm—James L. DeCesare

[57] ABSTRACT

An antiperspirant product contains as components at least one material selected from the group consisting of astringent antiperspirant compounds, a volatile silicone, a suspending agent, a waxy material, emollients, perfumes, and coloring agents used in making antiperspirants. The improvement relates to the formation of a gel by incorporating in the product a gelling agent which is an organic compound including polycyclic aromatic and steroidal groups linked through ester linkages. A method of forming thermally irreversible organosilicon gels is also described.

7 Claims, No Drawings

ORGANOSILICON GELS AND METHOD OF MAKING

BACKGROUND OF THE INVENTION

This invention relates to gel compositions and to a method of forming an organosilicon gel with a gelling agent which is a certain cholesteryl and cholestanyl ester of anthracene analogues and derivatives thereof.

A gel is a semisolid system having a high viscosity in the form of a jelly or paste. It is a two phase colloidal system consisting of a solid and a liquid in more solid form than a sol. It is believed that the initial step in forming a gel from an emulsoid begins with a fluid sol which includes concentrated droplets of disperse phase scattered throughout a dilute solution of a dispersion medium. Upon cooling the sol there is a disturbance of the equilibrium between the droplets and the surrounding dilute solution. The droplets draw the dilute solution into themselves, increase in size, and come into contact with one another forming cells like a honeycomb. This change results in a substantial decrease in fluidity which progresses to a sponge like structure representing a semi-solid jelly otherwise known as a gel. Continuation of the process results in the viscous particles uniting to form a continuous phase which encloses the droplets of what was previously the dispersion medium. The structure of the original emulsoid is thereby completely reversed with the more concentrated phase functioning as the dispersion medium while the more dilute phase is discontinuous.

A gel has also been defined as a crosslinked polymer network which is swollen in a liquid medium. The liquid prevents the polymer network from collapsing into a compact mass and the network in turn retains the liquid. The most familiar gel is the dessert JELLO ®, a trademark of the General Foods Corporation, White Pains, N.Y., in which the network constitutes polymers derived from animal protein gelatin whereas the liquid is colored flavored sweetened water. While some gels are crosslinked chemically by covalent bonds other gels are crosslinked physically by weaker forces such as hydrogen bonds and van der Waals forces. JELLO ® is a physically crosslinked gel which can be reversibly dissolved by moderate heating.

In U.S. Pat. No. 4,790,961 issued Dec. 13, 1988 there is described a thermally reversible gel and a method for the formation of gels of certain organic liquids by adding to the organic liquid a gelling agent which is a cholesteryl and cholestanyl ester of anthracene and anthraquinone analogues and derivatives thereof. The mixture is heated until homogeneous and upon cooling a gel is said to form. Exemplary of the organic liquids that are said to be capable of being gelled in accordance with the '961 patent are n-dodecane a saturated aliphatic hydrocarbon, and 4-heptanol and n-octanol which are aliphatic alcohols. While the disclosure of the '961 patent is primarily directed to the formation of gels of such organic liquids, the '961 patent does mention "silicone oils". However, in attempts to follow the teaching of the '961 patent it was found that gels of organosilicon compounds could not be formed in accordance with the teaching of the '961 patent. It was discovered that organosilicon gels could be formed nevertheless by a new and novel procedure which is beyond the scope of the '961 patent and which new and novel procedure constitutes the method of the present invention for the production of unique gels. In addition it was discovered that contrary to the teaching of the '961 patent that the gels which were formed were thermally irreversible rather than thermally reversible as specified in the '961 patent. Thus upon melting the gels of the present invention collapse to a cloudy white mixture which is transformed to a clear liquid containing suspended crystals of the gelling agent. Such new compositions are not taught in the '961 patent nor contemplated therein.

The gels of the present invention are further distinct from the gels of the '961 patent in that the instant gels are stable at temperatures much in excess of their initial temperature of gelation. Some gels produced in accordance with the present invention have been found to gel at temperatures above room or ambient temperature. Since the gels of the '961 patent are thermally reversible such gels are destroyed at temperatures in excess of 50–70 degrees Centigrade whereas the gels disclosed herein are stable at elevated temperatures in excess of one hundred degrees Centigrade.

Gelled antiperspirant formulations are not new as evidenced by U.S. Pat. No. 4,954,333 issued Sep. 4, 1990 in which dibenzylidene sorbitol is included as a gellant in a composition containing a silane. Novel gelled antiperspirant products however may be produced in accordance with the present invention by employing the gelators of the '961 patent in combination with certain siloxanes. It is also significant to note that unexpectedly the presence of solid particulate matter such as the antiperspirant active ingredient or the clay additive does not destroy the formation of the gel and has not been found to cause any disruption in the gel network.

SUMMARY OF THE INVENTION

This invention is directed to a method of forming an organosilicon gel with a gelling agent which is an organic compound including polycyclic aromatic and steroidal groups linked through ester linkages. The method involves mixing the gelling agent which is a solid in the form of crystals with an organosilicon compound, adding a volatile solvent such as chloroform to the mixture of the gelling agent and the organosilicon compound to dissolve the gelling agent and in order to form a homogeneous solution, heating the homogeneous solution of the gelling agent, the organosilicon compound and the volatile solvent to evaporate the volatile solvent, removing the volatile solvent from the homogeneous solution, and cooling the heated homogeneous solution or allowing the heated homogeneous solution to form an organosilicon gel.

As essential feature of the method in accordance with the present invention is the removal of the volatile solvent. This step is not taught in the prior art namely the '961 patent and provides for the successful formation of organosilicon gels as described herein. While cooling of the heated homogeneous solution often results in the formation of organosilicon gels, cooling to ambient temperatures is not always required as some gels have been formed merely upon removal of the volatile solvent.

In addition the invention relates to organosilicon gel compositions formed in accordance with the forming method as well as to an antiperspirant product containing as components thereof at least one material selected from the group consisting of astringent antiperspirant compounds, a volatile silicone, a suspending agent, a waxy material, emollients, perfumes, coloring agents, and other ingredients normally used in making antiperspirant products. The improvement in accordance with one embodiment of the present invention comprises the formation of a gelled antiperspirant product by utilizing as the gelling agent an organic compound which includes polycyclic aromatic and steroidal groups linked through ester linkages.

These and other features, objects and advantages of the present invention will become more apparent from a consideration of the following detailed description thereof.

DETAILED DESCRIPTION OF THE INVENTION

The gelling agent employed in the present invention is an organic compound which includes polycyclic aromatic and steroidal groups linked through ester linkages. More particularly the gelling agent is a compound having the formula $$R_1-(CH_2)_n-CO_2-R_2 \text{ or}$$

$$R_1-O-(CH_2)_n-CO_2R_2$$

in which $R_1$ is an anthracene analogue, an anthraquinone analogue, or substituted analogues thereof; $R_2$ is cholesteryl, cholestanyl or derivatives thereof; and n is zero or a whole number from two to twenty. More specifically the gelling agent is a compound having a formula selected from the group consisting of

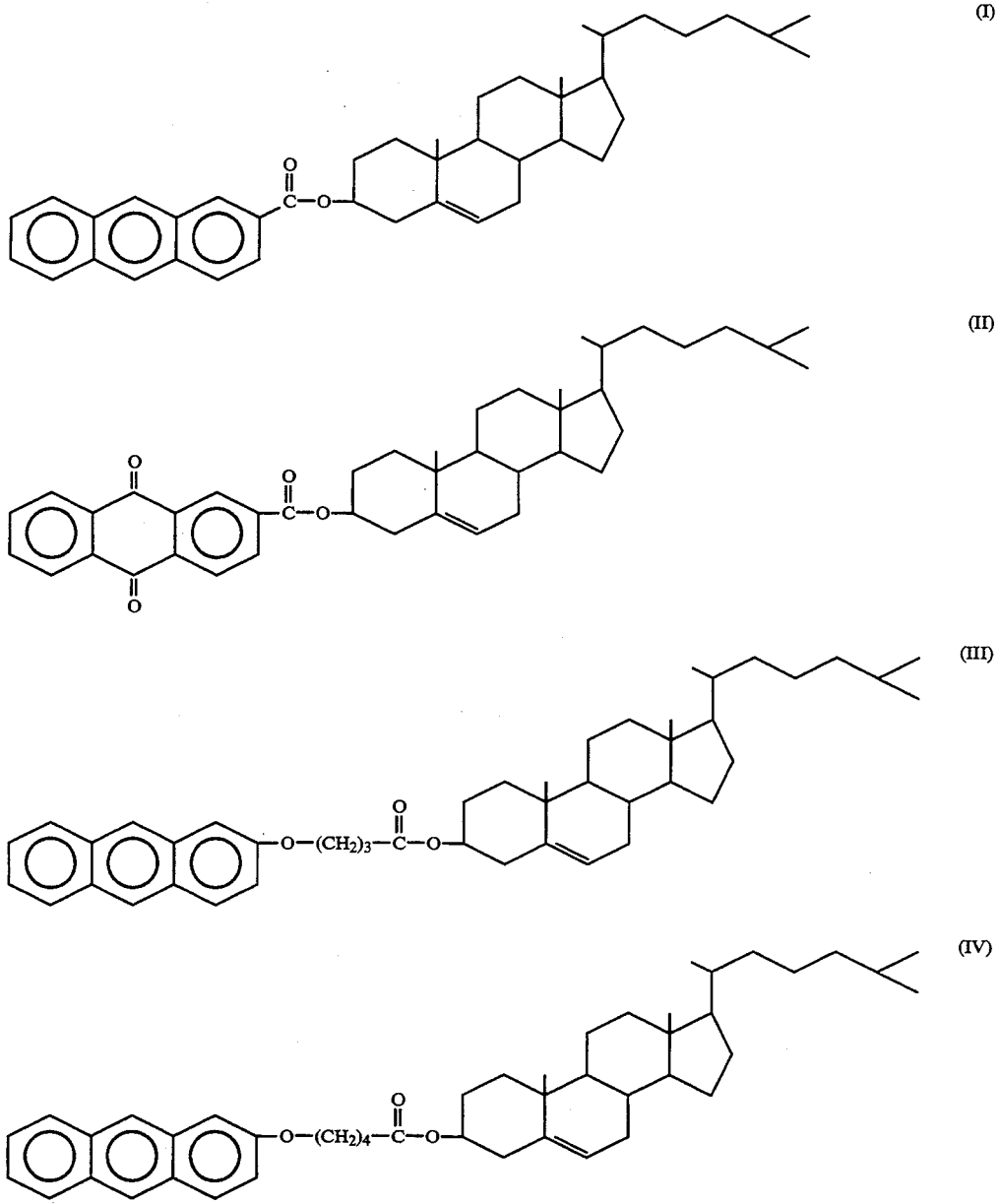

As noted previously there is described in U.S. Pat. No. 4,790,961 a process for forming gels of organic liquids by adding to the organic liquid a gelling agent which is a cholesteryl and cholestanyl ester of anthracene or anthraquinone analogues. In accordance with the procedure of the '961 patent a mixture of the material to be gelled and the gelling agent is heated until homogeneous and upon cooling a gel is said to form. Organosilicon compounds could not be gelled by this procedure.

It was however possible to achieve gel formation by adding a volatile organic solvent such as chloroform to a mixture of the gelling agent and the organosilicon compound in order to solubilize the gelling agent, heating the mixture of the organosilicon compound, the gelling agent, and the chloroform to remove the solvent from the mixture, cooling the mixture to ambient temperature and allowing the cooled mixture to form an organosilicon gel. This procedure is not disclosed in the '961 patent. While the '961 patent does teach the use of a solvent it does not teach removal of the solvent prior to cooling. This critical step in accordance with the procedure of the present invention has been found necessary and provides for gelation of organosilicon compounds, which contrary to the '961 patent are thermally irreversible rather than thermally reversible as taught therein.

The solvent which is used to predissolve the gelling agent is an organic solvent among which are halogenated organic compounds such as chloroform. Solvents such as ethers exemplary of which is tetrahydrofuran and aromatic hydrocarbon compounds such as toluene and benzene may also be used as the volatile solvent. The boiling point of each of these solvents is chloroform (61.2° C.); tetrahydrofuran (66° C.); toluene (110.7° C.); and benzene (80.1° C.), as is known in the art. The gelling agent is added to the organosilicon compound in an amount preferably less than about two percent by weight based on the weight of the organosilicon compound. One preferred gelling agent is cholesteryl anthraquinone-2-carboxylate hereinafter referred to as "CAQ" and which is shown structurally in Formula (II) above.

The term "organosilicon compound" as used herein is intended to include organic compounds of silicon such as organosilicon fluids and resins containing Si-C bonds. The term covers monomers such as organsilanes, organohalosilanes, organoalkoxysilanes and organoaminosilanes. Polymers such as polyorganosiloxanes, polyorganosilcarbanes, polyorganosiloxanes, polyorganosilthianes, and oligomers thereof are also included. Some specific examples of organosilicon fluids contemplated herein are alkali metal carboxylate siloxane fluids; alkylaralkyl functional siloxane fluids; alkylaralkylglycol functional siloxane fluids; alkyl and aryl methyl functional siloxane fluids; amide functional siloxane fluids; amideacetate functional siloxane fluids; amino endblocked siloxane fluids; aminofunctional siloxane fluids; carboxyfunctional siloxane fluids; chloroalkyl functional siloxane fluids; epoxy endblocked siloxane fluids; epoxy and epoxyglycol functional fluids; hexenyl functional siloxane fluids; hydrolyzates; mercaptofunctional siloxane fluids; methylester functional siloxane fluids; quaternary ammonium salts of silanes; polydimethylsiloxane fluids having a viscosity measured at twenty-five degrees Centigrade of 0.65 to about 300,000 centistokes, perfluorofunctional siloxane fluids; triacetoxysilanes; trialkoxysilanes; silanol fluids; silicone glycol and silicone glycolmethoxy copolymers; vinylsiloxanes; and zwitterionic functional siloxane fluids.

The organosilicon compound which is gelled in accordance with the present invention can also be a cyclic siloxane. Such compounds have the formula $[(CH_3)_2SiO]_x$ in which x is an integer of from three to ten. Some volatile cyclic siloxane compounds found to be especially useful are the tetramer octamethylcyclotetrasiloxane and the pentamer decamethylcyclopentasiloxane and mixtures thereof. These volatile cyclic polydimethylcyclosiloxane fluids have a viscosity ranging from about 2.5 to about 5.0 centistokes measured at twenty-five degrees Centigrade. Linear volatile siloxane fluids are further contemplated herein such as hexamethyldisiloxane which has a viscosity of about 0.65 centistokes as well as those linear volatile silicones conforming generally to the formula $(CH_3)_3SiO[Si(CH_3)_2O]_n\text{-}Si(CH_3)_3$ in which n is about three to nine.

Most preferably the organosilicon compound is a polysiloxane have the repeating unit

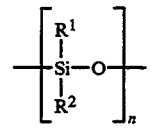

wherein n is an integer having a value greater than 1; $R^1$ is an alkyl radical containing 1 to 7 carbon atoms inclusive or a phenyl group; and $R^2$ is hydrogen, an alkyl radical containing 1 to 7 carbon atoms inclusive or a phenyl group. Illustrative polysiloxanes encompassed by the above formula are polydimethylsiloxane, polydiethylsiloxane, polymethlethyl siloxane, polymethylphenylsiloxane, polydiphenylsiloxanes, diphenylsilanediol and copolymers of two or more of the foregoing siloxanes. Particularly preferred organosilicon compounds which can be used are the linear volatile siloxane hexamethyldisiloxane, a linear siloxane having a viscosity of about 350 centistokes, phenylfunctional polydiorganosiloxanes, aminofunctional polydiorganosiloxanes, glycolfunctional polydiorganosiloxanes, methylhydrogen polysiloxanes, fluorosilicones, octamethylcyclotetrasiloxane, decamethylcyclopentasiloxane, and mixtures of octamethylcyclotetrasiloxane and decamethylcylopentasiloxane.

Because the present invention contemplates the application of the organosilicon gels in personal care formulations, an especially preferred compound is a siloxane having polar amine groups along the chain. Such groups have a profound effect on the deposition properties of the siloxane polymer and provide the polymer with an affinity for various surfaces. The amine functional siloxane polymer has the formula

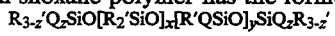

wherein R' denotes an alkyl group of 1 to 4 carbons, OH, an alkoxy group, or a phenyl group, with the proviso that at least 50 percent of the total R' groups are methyl; Q denotes an amine functional substituent of the formula —R"Z, wherein R" is a divalent alkylene radical of 3 to 6 carbon atoms or a radical of the formula —CH$_2$CH$_2$CH$_2$OCH$_2$—CHOHCH$_2$— and Z is a monovalent radical selected from the group consisting of —NR$_2$''', —NR'''(CH$_2$)$_n$NR$_2$'''; and

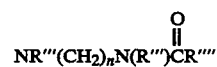

wherein R''' denotes hydrogen or an alkyl group of 1 to 4 carbons, R'''' denotes an alkyl group of 1 to 4 carbons and n is a positive integer from 2 to 6; z has a value of 0 or 1; x has an average value of 25 to 3000; y has an average value of 0 to 100 when z is 1, y has an average value of 1 to 100 when z is 0; with the proviso that in all cases y has an average value that is not greater than one tenth the average value of x.

The gels are prepared by adding a volatile organic solvent such as chloroform to a mixture of the organosilicon compound and the gelling agent to dissolve the gelling agent, evaporating the solvent by gentle heating and allowing the silicone to solidify, Gelation occurs by crystallization of the gelling agent from the silicone-solvent mixture. Because of the liquid crystalline nature of the gelling agent, the material orients into a fiber-like lattice with the silicone entrapped in the network. The gels are stable but heating or mechanical disruption can destroy the crystallinity releasing the silicone. Firmness and clarity of the gels is dependent upon the level of gelling agent which is employed and the particular nature of the silicone being gelled. Clear gels have been produced by the incorporation of about 0.5 percent by weight of gelling agent and decamethylcyclopentasiloxane. Translucent waxy-like gels have been obtained using about two percent by weight of the gelling agent a glycolfunctinal polydiorganosiloxane. The gels have utility in personal care products for antiperspirant applications. The gels can be produced from a variety of reactive as well as non-reactive organosilicon compounds as indicated in detail above.

The following examples further illustrate the concepts embodied in the present invention.

EXAMPLE I

PREPARATION OF CHOLESTERYL ANTHRAQUINONE-2-CARBOXYLATE (CAQ)

Attempts to synthesize CAQ as reported in U.S. Pat. No. 4,790,961 produced low yields of CAQ. This was attributed to the low solubility of the starting material anthraquinone carboxylic acid in benzene the solvent of choice. Tetrahydrofuran (THF) was determined to be a superior solvent for the reaction sequence and was used.

Step 1

Into a three-necked 100 ml flask equipped with a thermometer, condenser and nitrogen line a mixture of 1.01 grams of anthraquinone carboxylic acid (4 mmoles) and 4.54 grams of oxalyl chloride (35.8 mmoles) in 87 ml of dry THF was stirred and heated (45°-50° C.) in a dry atmosphere for 1 hour and stirred at ambient temperature for 16 hours. THF and excess oxalyl chloride were removed on a rotary evaporator. Residual oxalyl chloride was removed by heptane washing of the crude acid chloride which is a yellow solid residue and inert atmosphere filtration.

Step 2

1.55 grams of cholesterol (4 mmoles), 400 microliters pyridine (5 mmoles) and 56 ml dry THF were added to the anthraquinone acid chloride and the mixture stirred at ambient temperature for 16 hours under a dry atmosphere.

PURIFICATION

All starting materials, the acid chloride intermediate and the product CAQ are soluble in THF. The by-product in the second step pyridine hydrochloride is not soluble in THF and was removed by filtering. The yellow solid product was obtained after THF was removed on a rotary evaporator. Unreacted anthraquinone carboxylic acid was selectively precipitated and removed from a chloroform solution containing the product. A 20-25 percent solution of CAQ in chloroform was passed through a silica column to separate pure CAQ from unreacted anthraquinone carboxylic acid, anthraquinone acid chloride and cholesterol. The acid, acid chloride and cholesterol adsorb onto silica more strongly than the product. The product was recrystallized from chloroform/methanol.

VERIFICATION OF PRODUCT

IR analysis of the product showed a disappearance of the acid carbonyl absorption at 1702 cm−1 due to the starting material anthraquinone carboxylic acid and the appearance of the ester carbonyl absorption at 1723 cm−1 from the ester linkage in the product. $^1$H-NMR analysis of the product showed a shift in the signal due to the alkenyl proton from 5.3 ppm for the starting material cholesterol alone to 5.4 ppm in the product due to the more polar environment in the CAQ molecule. The material displayed color changes upon heating (liquid crystalline behavior) and had a melting point of 230° C.

EXAMPLE II

Chloroform was added to 0.05 grams of CAQ in 2.5 grams of dimethylcyclosiloxanes until the CAQ was dissolved. The dimethylcyclosiloxanes contained 5.7 percent of the trimer, 55.7 percent of the tetramer, 32.55 percent of the pentamer, 4.98 percent of the hexamer, 0.66 percent of the heptamer, 0.19 percent of the octamer and 0.05 percent of the nonamer. The solution was heated to evaporate the chloroform. A gel formed by removing the chloroform solvent at a temperature above ambient.

EXAMPLE III

Chloroform was added to 0.011 grams of CAQ in 0.52 grams of polydimethylsiloxane fluid having a viscosity of 350 centistokes measured at 25° C. until the CAQ was dissolved. The solution was heated to evaporate the chloroform. A gel formed by removing the chloroform solvent at a temperature above ambient.

EXAMPLE IV

Chloroform was added to 0.010 grams of CAQ in 0.50 grams of hexamethyldisiloxane having a viscosity of 0.65 centistokes measured at 25° C. until the CAQ was dissolved. The solution was heated to evaporate the chloroform. Cooling of the solution to ambient temperature led to gel formation.

Antiperspirant compositions may be produced in accordance with the present invention and preferably contain about fifteen to fifty weight percent of an astringent antiperspirant compound, about ten to eighty weight percent of a volatile silicone carrier, and about three to five weight percent of a suspending agent. The volatile cyclic and volatile low viscosity linear silicones have been described in detail above. Nonvolatile silicones and functional siloxanes described above may also be included as emollients in deodorants products.

Any conventional astringent antiperspirant compound can be used in accordance with the present invention. In general such materials comprise inorganic and organic salts of aluminum, zirconium, and zinc and mixtures thereof. Representative compounds are described throughout the patent literature in U.S. Pat. No. 4,280,994 issued Jul. 28, 1981; U.S. Pat. No. 4,369,173 issued Jan. 18, 1983; U.S. Pat. No. 4,425,328 issued Jan. 10, 1984; U.S. Pat. No. 4,725,432 issued Feb. 16, 1988; and U.S. Pat. No. 4,822,603 issued Apr. 18, 1989. Examples of such astringent antiperspirant compounds are aluminum chloride, aluminum chlorohydrate, aluminum dichlorohydrate, aluminum-zirconium chlorohydrate, aluminum chlorohydrex, aluminum-zirconium trichlorohydrate, aluminum-zirconium pentachlorohydrate, aluminum-zirconium tetrachlorohydrex glycine, aluminum-zirconium octachlorohydrate, aluminum sesquichlorohydrate, aluminum sulfate, zinc sulfate, zirconium chlorohydrate, aluminum-zirconium chlorohydroglycine, zirconium hydroxychloride, zinc sulfocarbolate, aluminum bromide, zinc phenolsulfonate and aluminum bromohydrate.

Emollients, perfumes and other ingredients normally used in making antiperspirant products are well known in the art and are described throughout the patent literature in the previously mentioned U.S. Pat. Nos. 4,280,994; 4,425,328; 4,725,432; and 4,822,603.

The use of suspending agents in antiperspirant products is conventional in the art as represented by U.S. Pat. No. 4,904,463 issued Feb. 27, 1990. As noted in the —463 patent clay minerals such as hectorite and bentonite as a suspending agent require that the clay mineral be treated with a cationic surfactant material to render the clay mineral hydrophobic. Ditallow dimethyl ammonium chloride is one cationic surfactant found most suitable for such treatments. In addition to requiring this pre-hydrophobing treatment, systems containing these clay minerals may require a separate activator such as ethanol or propylene carbonate which enables the hydrophobically treated clay material to suspend the antiperspirant compound in the carrier fluid.

Waxy materials which may be employed in accordance with the present invention include waxes, gums, resins, polymers, starches and elastomers. Exemplary waxes are insect and animal waxes such as beeswax and spermaceti; vegetable waxes such as candelilla, carnauba, Japan wax, Ouricury, Douglas-fir bark wax, rice-bran wax, jojoba wax, castor wax and bayberry wax; mineral waxes such as montan wax, peat wax, ozokerite and ceresin; petroleum waxes such as paraffin wax; synthetic waxes such as polyethylene waxes, Fischer-Tropsch waxes, chemically modified hydrocarbon waxes and substituted amide waxes; and silicone wax. Reference may be had to U.S. Pat. No. 3,395,941 issued Jul. 30, 1968 describing a silicone wax which is an organosilicon block copolymer; and U.S. Pat. No. 3,563,941 issued Feb. 16, 1971 describing a silicone-carnauba wax copolymer. In addition there may be employed wax-like solids such as steary alcohol, cetyl alcohol, myristyl alcohol and palmitic acid; gums such as celullosic gums and alignate gums; polymers such as polyvinyl alcohol; and resin such as polyvinylpyrrolidone. Reference may be had to U.S. Pat. No. 4,822,603, issued Apr. 18, 1989 wherein many of such materials are described in detail.

The following examples are set forth in order to illustrate gelled antiperspirant formulations prepared in accordance with the present invention.

EXAMPLE V

Chloroform was added to 0.01 grams of CAQ in 0.5 grams of an antiperspirant formulation containing by weight 47.05 percent ethanol, 23,53 percent of $ZrOCl_2 8H_2O$ and 29.42 percent of aluminum chlorohydrate. An antiperspirant gel formed upon removal of chloroform.

EXAMPLE VI

Chloroform was added to 0.01 grams of CAQ in 0.5 grams of an antiperspirant formulation containing by weight seventy-five percent of a cyclic siloxane, five percent of BENTONE® a collodial clay and trademark of the National Lead Company Charleston, W. Va., and twenty percent of aluminum zirconium tetrachlorohydrex glycine. An antiperspirant gel formed upon removal of chloroform.

The following additional examples are set forth in order to illustrate further gelled organosilicon formulations prepared in accordance with the present invention.

EXAMPLE VII

Examples III and IV were repeated except that in each instance the organosilicon compound which was employed was (i) a methylhydrogen functional polysiloxane, (ii) two phenylmethylpolysiloxanes, (iii) two amine functional polysiloxanes, and (iv) an alkylmethyl polysiloxane. Gels were formed with each of the six organosilicon compounds.

EXAMPLE VIII

In an effort to prepare organosilicon gels in accordance with the teaching of U.S. Pat. No. 4,790,961, there was placed in a vial 0.01 grams of the gelling agent CAQ. To the vial was added 0.5 grams of the dimethylcyclosiloxanes of Example II. The siloxane fluid containing the crystals of gelling agent was heated in accordance with the procedure of the '961 patent. However the gelling agent CAQ was found not to dissolve in accordance with the teaching in the '961 patent. For the purpose of illustrating the improvement provided by the present invention, there was added one gram of the volatile organic solvent chloroform which is a good solvent for the gelator CAQ. The CAQ was found to dissolve upon the addition of the volatile solvent. The solution was heated to remove the chloroform and a gel formed upon removal of the solvent. This indicates that while organic compounds may be gelled in accordance with the procedure of the —961 patent, that procedure and that patent are not specific to organosilicon compounds. Thus the present invention is directed to special procedures which have been found to be required in order to provide for the gelation of organosilicon materials. Such procedure as noted above requires the addition of a volatile solvent such as chloroform and its removal and such steps are not described in the prior art nor would such special steps inherently follow therefrom.

The '961 patent requires that for a material to be capable of being gelled in accordance with that procedure, the material is required to be a poor solvent for the gelling agent at ambient temperature but the material must be capable of dissolving the gelling agent at elevated temperature. Organosilicon compounds have been found to be poor solvents for the gelling agent at both ambient and elevated temperatures. This necessitates a departure from the teaching of the '961 patent and requires the addition of chloroform which is a good solvent for the gelling agents of the —961 patent. However as noted previously, the chloroform must be removed in order for the gel to form and this procedure and improvement is not taught in the prior art including the '961 patent. The formation of organsilicon gels is also unique to the extent that where cooling is required to form a gel, the temperature are generally much in excess of the temperatures required for organic materials and as set forth in the '961 patent.

It will be apparent from the foregoing that many other variations and modifications may be made in the compounds, compositions and methods described herein without departing substantially from the essential features and concepts of the present invention. Accordingly it should be clearly understood that the forms of the invention described herein are exemplary only and are not intended as limitations on the scope of the present invention as defined in the appended claims.

That which is claimed is:

1. A method of forming a thermally irreversible organosilicon gel comprising mixing a gelling agent with an organosilicon compound, adding a volatile solvent to the mixture of the gelling agent and the organosilicon compound to dissolve the gelling agent, the solvent being selected from the group consisting of halogenated organic compounds, ethers and aromatic compounds, forming a homogeneous solution of the gelling agent, the organosilicon compound and the volatile solvent, heating the homogeneous solution of the gelling agent, the organosilicon compound and the volatile solvent to evaporate the volatile solvent, removing the volatile solvent from the homogeneous solution, and allowing the heated homogeneous solution to form an organosilicon gel, the gelling agent being an organic compound which includes polycyclic aromatic and steroidal groups linked through ester linkages and having a formula selected from the group consisting of $R_1O(CH_2)_nCO_2R_2$ and $R_1(CH_2)_nCO_2R_2$ wherein $R_1$ is an anthracene analogue, an anthraquinone analogue, or substituted analogues thereof; $R_2$ is cholesteryl, cholestanyl, or derivatives thereof; and n is zero or a whole number from two to twenty.

2. The method of claim 1 in which the organic compound gelling agent has a formula selected from the group consisting of

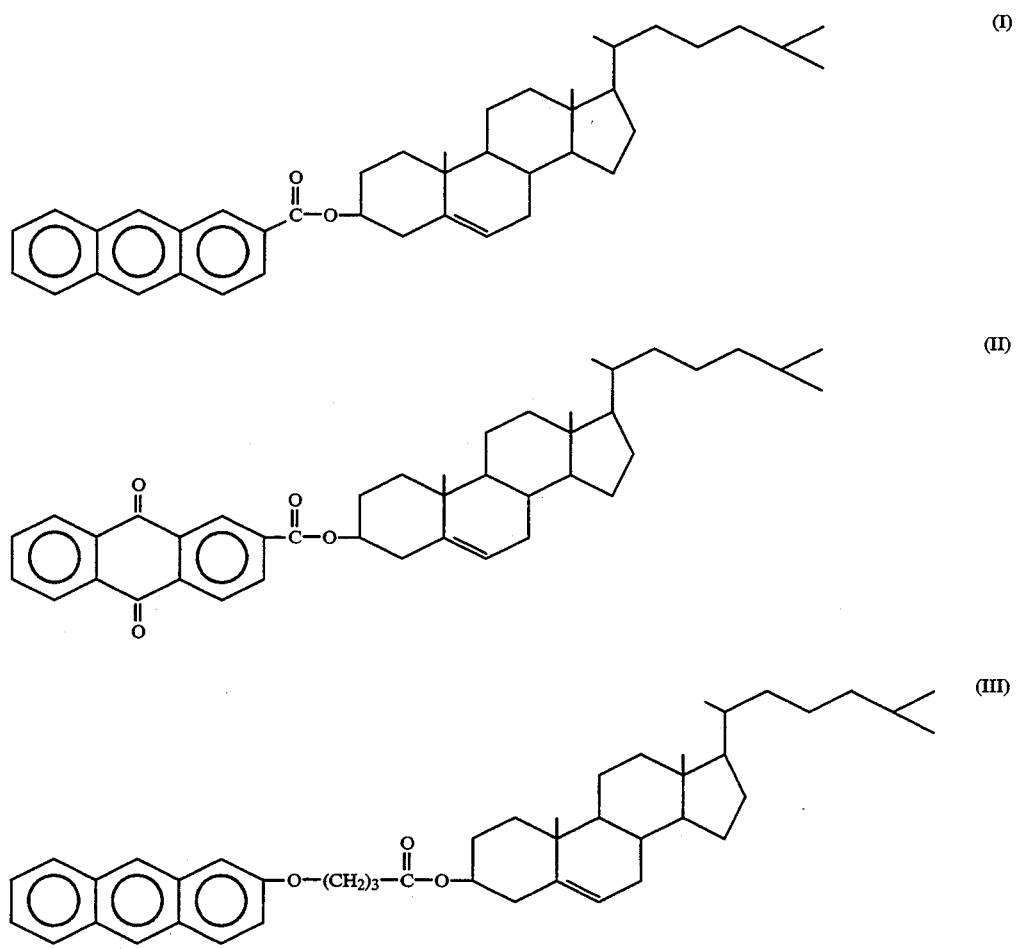

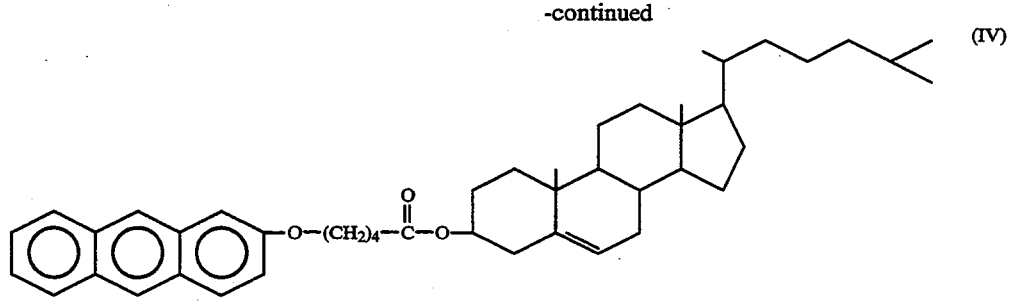

(IV)

3. The method of claim 1 in which the organosilicon compound is selected from the group consisting of linear siloxanes and cyclic siloxanes.

4. The method of claim 3 in which the organosilicon compound is a cyclic siloxane having the formula $[(CH_3)SiO]_x$ in which x is an integer having a value of three to ten.

5. The method of claim 3 in which the organosilicon compound is a linear siloxane selected from the group consisting of polydimethylsiloxanes, phenylfunctional polydiorganosiloxanes, aminofunctional polydiorganosiloxanes, polydiorganosiloxanes, glycolfunctional polydiorganosiloxanes, methylhydrogen polysiloxanes, alkylmethyl polysiloxanes and fluorosilicones.

6. A thermally irreversible organosilicon gel formed in accordance with the method of claim 1.

7. A method of forming a thermally irreversible organosilicon gel comprising mixing a gelling agent with an organosilicon compound, adding a volatile solvent to the mixture of the gelling agent and the organosilicon compound to dissolve the gelling agent, the solvent being chloroform, forming a homogeneous solution of the gelling agent, the organosilicon compound and the volatile solvent, heating the homogeneous solution of the gelling agent, the organosilicon compound and the volatile solvent to evaporate the volatile solvent, removing the volatile solvent from the homogeneous solution, and allowing the heated homogeneous solution to form an organosilicon gel, the gelling agent being cholesteryl anthraquinone-2-carboxylate.

* * * * *